United States Patent
Cunnane

(10) Patent No.: US 9,440,048 B2
(45) Date of Patent: Sep. 13, 2016

(54) CATHETER ASSEMBLY WITH CUFF DEPLOYMENT DEVICE

(71) Applicant: Connor Cunnane, Bloomington, IN (US)

(72) Inventor: Connor Cunnane, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 823 days.

(21) Appl. No.: 13/723,414

(22) Filed: Dec. 21, 2012

(65) Prior Publication Data

US 2014/0180247 A1    Jun. 26, 2014

(51) Int. Cl.
*A61M 31/00* (2006.01)
*A61M 29/00* (2006.01)
*A61M 25/04* (2006.01)

(52) U.S. Cl.
CPC ................................. *A61M 25/04* (2013.01)

(58) Field of Classification Search
CPC ........... A61M 25/04; A61M 25/1018; A61M 2025/1043; A61M 2025/1054; A61M 25/10; A61M 2025/0175
USPC ....................................................... 604/509
See application file for complete search history.

(56) References Cited

U.S. PATENT DOCUMENTS

| 4,126,134 A | * | 11/1978 | Bolduc ................. A61M 31/00 604/201 |
| 4,955,890 A | * | 9/1990 | Yamamoto ....... A61B 17/32093 604/175 |
| 5,190,529 A | | 3/1993 | McCrory et al. |
| 7,753,889 B2 | | 7/2010 | Rosenberg |
| 7,811,257 B2 | | 10/2010 | Saab |
| 7,947,019 B2 | | 5/2011 | Perchik et al. |
| 8,142,401 B2 | | 3/2012 | Rosenberg |
| 8,147,459 B2 | | 4/2012 | Rosenberg et al. |
| 2004/0186461 A1 | | 9/2004 | DiMatteo |
| 2007/0038178 A1 | * | 2/2007 | Kusleika ................. A61F 2/013 604/103.03 |
| 2010/0210923 A1 | * | 8/2010 | Li ......................... A61B 5/042 600/301 |
| 2012/0209206 A1 | | 8/2012 | Scandone, Jr. |
| 2012/0245528 A1 | | 9/2012 | Lareau et al. |

* cited by examiner

Primary Examiner — Jason Flick
(74) Attorney, Agent, or Firm — Liell & McNeil

(57) ABSTRACT

A catheter assembly includes a catheter having an elongate tubular body defining a lumen extending from an open proximal end to an open distal end. A cuff deployment device is concentrically supported on the elongate tubular body and is movable along a longitudinal axis of the elongate tubular body. The cuff deployment device includes a deployment mechanism having an actuated position and a non-actuated position. A cuff has a hollow cylindrical body defining an internal catheter engagement surface. The catheter assembly has a first configuration in which the deployment mechanism is in the non-actuated position and the cuff is supported by and movable with the cuff deployment device, and a second configuration in which the deployment mechanism is in the actuated position and the cuff is concentrically mounted at a fixed axial location of the elongate tubular body and is free of contact with the cuff deployment device.

20 Claims, 2 Drawing Sheets

CATHETER ASSEMBLY WITH CUFF DEPLOYMENT DEVICE

TECHNICAL FIELD

The present disclosure relates generally to a cuff deployment device for a catheter assembly, and more particularly to a cuff deployment device for deploying a cuff at a fixed axial location along a catheter.

BACKGROUND

Catheters may be used to provide vascular access for a number of different procedures. For example, catheters may be inserted into a blood vessel to draw blood or deliver medications into the bloodstream of a patient. Although many catheters are intended for short-term use, some vascular access is needed for a longer period of time. For such long-term access, which may include days, weeks, or years, a central access catheter may be used to provide a more secure venous access. Typically, the central access catheter is inserted into a major vein in the neck, arms, or legs, and may be repeatedly accessed over the necessary period of time. Tunneled catheters may be used in these instances to protect the catheter from moisture and inadvertent pulling. A tunneled catheter is positioned through a subcutaneous tunnel of the patient and includes a cuff for securing the position of the catheter within the subcutaneous tunnel.

Typically, the cuff is made from a porous tissue ingrowth material and is provided at a fixed axial location along the catheter. Unfortunately, due to the various tunnel sizes and configurations, a similar cuff positioning may not be appropriate for different procedures. Additionally, cuff placement preferences may vary by clinician. As such, a supply of catheters having cuffs fixed at varying axial locations along the respective catheters may be necessary. Additionally, or alternatively, clinicians may trim the distal end of the catheter to achieve a desired cuff-to-distal tip distance. However, trimming the distal end of a catheter may remove desired distal tip features, including an atraumatic profile, which may render the catheter placement procedure more difficult.

U.S. Patent Application Publication No. 2012/0209206 to Scandone, Jr. (hereinafter Scandone) teaches a catheter securable cuff having two body portions securable to each other about the catheter body at a location selected by a practitioner. In particular, the two cuff portions are separately slidable along the catheter prior to coupling, but include complementary catheter-gripping sections that cooperate with each other to grip the catheter upon assembly. Although the catheter securable cuff of Scandone may provide a means for selecting and fixing cuff placement relative to a catheter, it should be appreciated that there is a continuing need for efficient and effective catheter assemblies for catheter placement procedures.

The present disclosure is directed toward one or more of the problems or issues set forth above.

SUMMARY OF THE DISCLOSURE

In one aspect, a catheter assembly includes a catheter having an elongate tubular body defining a lumen extending from an open proximal end of the elongate tubular body to an open distal end of the elongate tubular body. A cuff deployment device is concentrically supported on the elongate tubular body and is movable along a longitudinal axis of the elongate tubular body. The cuff deployment device includes a deployment mechanism having an actuated position and a non-actuated position. The catheter assembly also includes a cuff having a hollow cylindrical body defining an internal catheter engagement surface. The catheter assembly has a first configuration in which the deployment mechanism is in the non-actuated position and the cuff is supported by and movable with the cuff deployment device, and a second configuration in which the deployment mechanism is in the actuated position and the cuff is concentrically mounted at a fixed axial location of the elongate tubular body and is free of contact with the cuff deployment device.

In another aspect, a cuff deployment device for a catheter assembly includes a hollow cylindrical housing having an open proximal deployment end and a distal end. A tubular plunger defines an inner catheter engagement surface and has an actuation end supported within an opening through the distal end of the hollow cylindrical housing. The tubular plunger is telescopically movable with respect to the hollow cylindrical housing. A cuff having a hollow cylindrical body defining an internal catheter engagement surface is telescopically received within the hollow cylindrical housing.

A method of implanting the catheter assembly set forth above in a patient vasculature includes a step of sliding the cuff deployment device toward a fixed axial location of the elongate tubular body while the catheter assembly is in the first configuration. The catheter assembly is moved from the first configuration to the second configuration by actuating the deployment mechanism. The method also includes removing the cuff deployment device from the elongate tubular body of the catheter.

DETAILED DESCRIPTION

Figure 1:
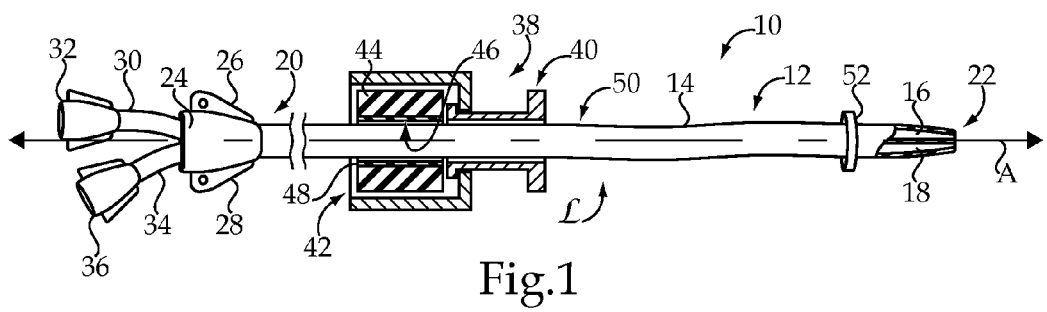
FIG. 1 is a partially sectioned side diagrammatic view of a catheter assembly having a cuff deployment device supported thereon, shown in a first configuration, according to one embodiment of the present disclosure.

Referring to FIG. 1, there is shown a catheter assembly 10 according to one embodiment of the present disclosure. The catheter assembly 10 generally includes a catheter 12 having an elongate tubular body 14 defining a first lumen 16 and a second lumen 18, with both lumens 16 and 18 extending from an open proximal end 20 of the elongate tubular body 14 to an open distal end 22 of the elongate tubular body 14. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

The elongate tubular body 14 may range in length from several inches to several feet long, and may have a catheter wall outer diameter that is orders of magnitude smaller than its length. The elongate tubular body 14 may be made from a common medical tube material, such as, for example, a plastic, rubber, or other polymer, such that the catheter 12 exhibits both stiffness, or firmness, and flexibility. The catheter 12, which may be used to provide central venous access, may include any of a variety of known configurations. According to some examples, the catheter 12 may include a tapered distal segment and/or may include a lubricious coating to facilitate movement of the catheter 12 through the vasculature, or other bodily lumens, of a patient.

As shown, the catheter 12 may be a dual lumen catheter. In particular, the elongate tubular body 14 may define two separate lumens, i.e., the first lumen 16 and the second lumen 18. However, some alternative embodiments may include a single lumen catheter, while other alternative embodiments may include various multiple lumen catheters. Although the first and second lumens 16 and 18 are shown extending from the open proximal end 20 to the open distal end 22, the catheter 12 may include lumens extending only partially along an axial length of the catheter 12. Although not shown, the catheter 12 may include lateral openings or side ports, as necessary, depending on the particular application. One or both of the lumens 16 and 18 may be configured to advance over a wire guide, or telescopically receive a wire guide, as is useful in known procedures.

A manifold 24 may be attached at the open proximal end 20 and may include a pair of suture wings 26 and 28 for securing a position of the manifold 24 relative to a patient. Although not shown, it should be appreciated that the manifold 24 may define a first fluid channel for fluidly connecting the first lumen 16 with a first extension tube 30. The first extension tube 30 may include a first connecting device 32 defining a first hub of the catheter 12. The manifold 24, which may be a relatively rigid component made from a common medical grade material, may define a second fluid channel for fluidly connecting the second lumen 18 of the catheter 12 with a second extension tube 34. The second extension tube 34 may include a second connecting device 36 defining a second hub of the catheter 12. Although not shown, clamps, or other similar devices, may be provided for selectively closing off fluid flow through a respective one of the extension tubes 30 and 34 in a known manner. It should also be appreciated that connections or attachments between components of the catheter assembly 10 may be made using attachment means known to those skilled in the art.

The catheter assembly 10 also includes a cuff deployment device 38 concentrically supported on the elongate tubular body 14. The cuff deployment device 38 is movable along a longitudinal axis A of the elongate tubular body 14 of the catheter 12 and includes a deployment mechanism 40 having an actuated position and a non-actuated position. In particular, the deployment mechanism 40 of the cuff deployment device 38 is movable from a non-actuated position to an actuated position to deploy a cuff 42 at a selected axial location L of the catheter 12. The cuff 42, which will be discussed below in greater detail, has a hollow cylindrical body 44 defining an internal catheter engagement surface 46. As should be appreciated, the cuff deployment device 38 and cuff 42 are hollow, or otherwise shaped, to facilitate the positionings described herein relative to the catheter 12.

Figure 2:
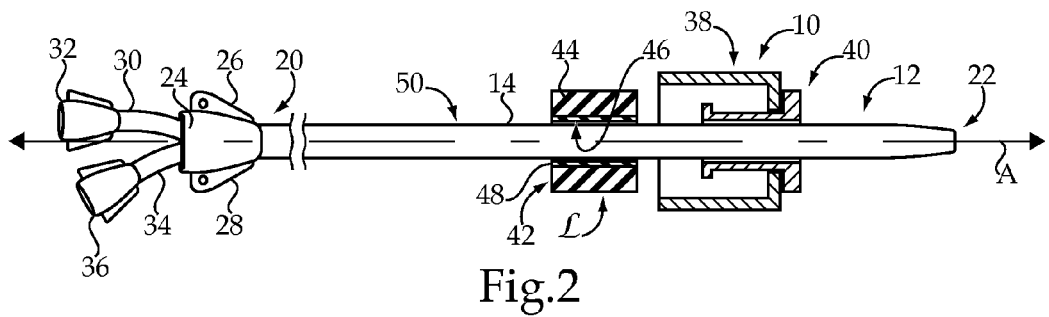
FIG. 2 is a partially sectioned side diagrammatic view of the catheter assembly of FIG. 1, shown in a second configuration.
Figure 3:
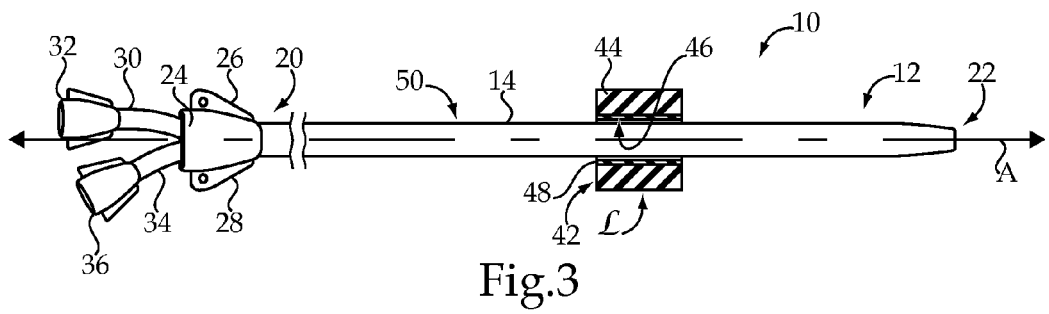
FIG. 3 is a partially sectioned side diagrammatic view of the catheter assembly of the previous FIGS., shown in a third configuration.

The catheter assembly 10 has a first configuration, as shown in FIG. 1, in which the deployment mechanism 40 is in the non-actuated position and the cuff 42 is supported by and movable with the cuff deployment device 38. The catheter assembly 10 also has a second configuration, as shown in FIG. 2, in which the deployment mechanism 40 is in the actuated position and the cuff 42 is concentrically mounted at the fixed axial location L of the elongate tubular body 14. According to the second configuration, the cuff 42 is released from, and is free of contact with, the cuff deployment device 38. According to some embodiments, an adhesive 48 may be provided on the internal catheter engagement surface 46 of the cuff 42 such that the adhesive 48 contacts an external surface 50 of the elongate tubular body 14 to maintain a desired positioning of the cuff 42, such as at the fixed axial location L selected by a clinician. As shown in FIG. 3, the catheter assembly 10 also has a third configuration in which the cuff 42 is concentrically mounted at the fixed axial location L of the elongate tubular body 14 and the cuff deployment device 38 is removed from the elongate tubular body 14 of the catheter 12.

Returning to FIG. 1, the catheter assembly 10 may also include a concentrically mounted end stop 52 positioned distally along the elongate tubular body 14 of the catheter 12 relative to the cuff deployment device 38. The concentrically mounted end stop 52, which may include a clip, clamp, or the like, may be configured to restrict distal movement of the cuff deployment device 39 beyond the end stop 52 in the first configuration of the catheter assembly 10. After the cuff 42 has been deployed using the cuff deployment device 39 and is positioned at the fixed axial location L, however, the end stop 52 may be removed such that the cuff deployment device 38 may also be removed from the catheter 12. For example, with the end stop 52 removed, the cuff deployment device 38 may be advanced distally along the catheter 12 and removed from the catheter 12 at the open distal end 22 thereof.

Figure 4:
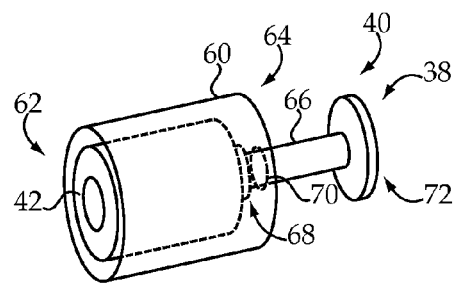
FIG. 4 is a perspective view of the cuff deployment device of FIGS. 1 and 2.

Turning now to FIG. 4, the cuff deployment device 38, according to the exemplary embodiment, generally includes a cylindrical housing 60 configured to telescopically receive the cuff 42. The cylindrical housing 60 has an open proximal deployment end 62, which facilitates insertion and removal of the cuff 42, and a distal end 64. The deployment mechanism 40 may include a hollow tubular plunger 66 having an actuation end 68 configured to contact the cuff 42 through an opening 70 through the distal end 64 of the cylindrical housing 60. The plunger 66 also has a user engagement end 72, which may be grasped by a clinician to move the plunger 66 between the actuated and non-actuated positions. As shown, the user engagement end 72 of the plunger 66 may be closer to the distal end 64 of the cylindrical housing 60 in the actuated position than in the non-actuated position. Although a particular embodiment is shown, it should be appreciated that alternative deployment devices capable of repositioning the cuff 42 prior to deployment are contemplated. Further, alternative deployment mechanisms, in addition to plunger-type devices, are also contemplated.

Figure 5:
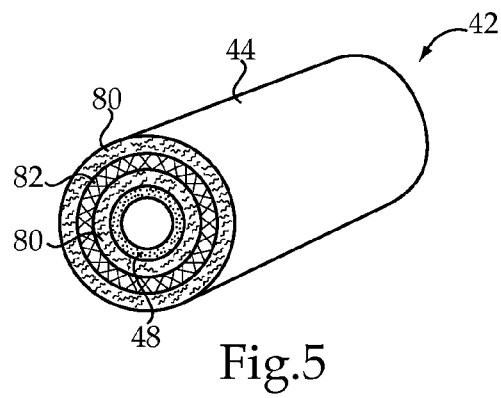
FIG. 5 is a perspective view of an exemplary cuff for use with the catheter assembly of the previous FIGS., according to the first configuration of the catheter assembly.
Figure 6:
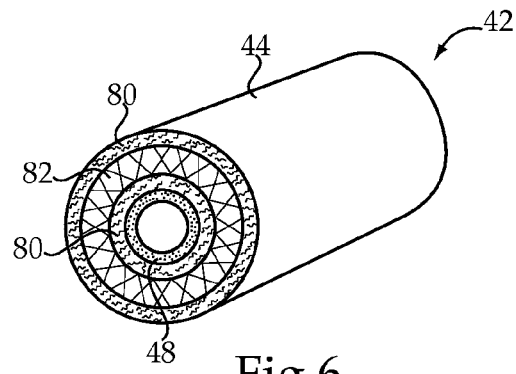
FIG. 6 is perspective view of the exemplary cuff of FIG. 5, shown according to the second configuration of the catheter assembly.

Referring to the exemplary embodiments of FIGS. 5 and 6, the cuff 42 may generally include a hollow cylindrical body 44. According to a specific example, the hollow cylindrical body 44 may include a porous tissue ingrowth material 80, which is known to those skilled in the art, surrounding a shape memory material 82. In particular, the shape memory material 82, which may include a self-expanding stent, may be provided between an outer layer of porous tissue ingrowth material 80 and an inner layer of porous tissue ingrowth material 80. According to some embodiments, an innermost layer, defining the internal catheter engagement surface 46 of the cuff 42 may include the medical adhesive 48, described above. The shape memory material 82, which may include nitinol, may be provided to facilitate expansion, such as radial expansion, of the cuff 42 in the second configuration of the catheter assembly 10. More specifically, the cuff 42 may have a restricted position, as shown in FIG. 5, which is maintained using the cylindrical housing 60, and an expanded position, as shown in FIG. 6, in which the cuff 42 is removed from the cylindrical housing 60 and the shape memory material 82 is permitted to return to a preformed, expanded shape. This self-expanding feature may assist in contacting the external surface 50 of the catheter 12 with the adhesive layer 48 of the cuff 42, although contact or pressure by the clinician may be required.

INDUSTRIAL APPLICABILITY

The present disclosure is generally applicable to medical devices for use in percutaneous vascular procedures, or other procedures involving cavities, ducts, or canals of a patient. More specifically, the present disclosure is applicable to catheter assemblies that may be used for vascular access. Yet further, the present disclosure is applicable to catheters that may be tunneled for long-term vascular access. Such tunneled catheters generally include a cuff that stimulates tissue growth to help secure the tunneled position of the catheter.

Referring generally to FIGS. 1-7, a catheter assembly 10 generally includes a catheter 12 having an elongate tubular body 14 defining first and second lumens 16 and 18 extending from an open proximal end 20 to an open distal end 22. The catheter assembly 10 also includes a cuff deployment device 38 concentrically supported on the elongate tubular body 14. According to an exemplary embodiment, the cuff deployment device 38 generally includes a cylindrical housing 60 configured to telescopically receive a cuff 42. A deployment mechanism 40 may include a tubular plunger 66 supported on the cylindrical housing 60 and configured to contact and deploy the cuff 42.

Figure 7:
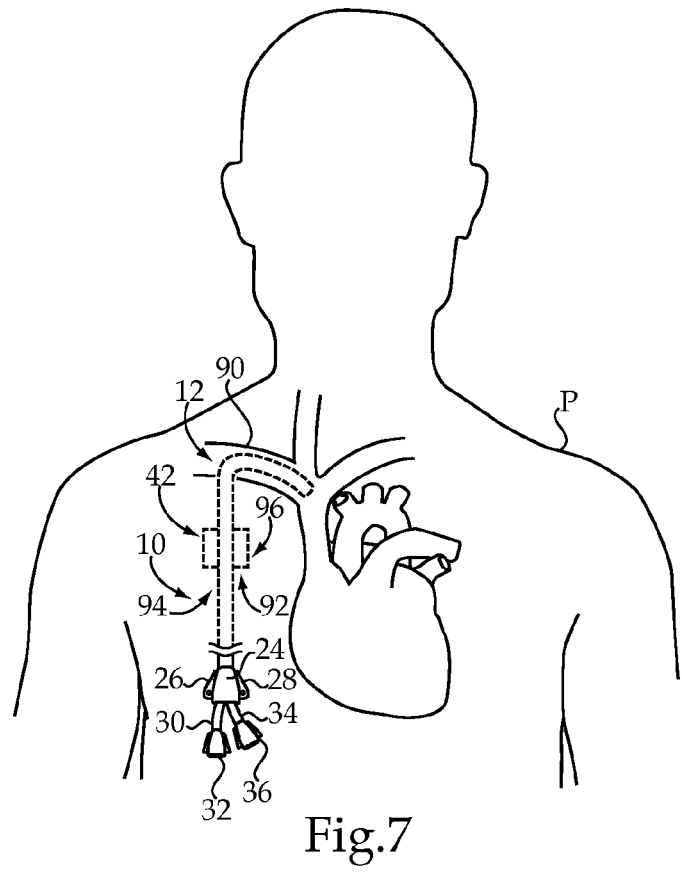
FIG. 7 is a diagrammatic view of the catheter assembly of the previous FIGS., depicted as an indwelling tunneled catheter, relative to a patient.

With particular reference to FIG. 7, a percutaneous vascular access procedure using the catheter assembly 10 of FIG. 1 will be described with reference to a vascular structure 90 of a patient P. In particular, a method of tunneling a portion of the catheter assembly 10 will be described. At the beginning of the procedure, the clinician may determine a desirable fixed axial location L along the catheter 12 for the cuff 42. In particular, the clinician may position the catheter assembly 10 relative to the patient P at the tunneling site to appropriately determine, based on the tunnel size and configuration for patient P, the desired fixed axial location L for the cuff 42.

The cuff deployment device 38 may then be slid toward the desired fixed axial location L while the catheter assembly 10 is in the first configuration of FIG. 1. The catheter assembly 10 may then be moved from the first configuration of FIG. 1 to the second configuration of FIG. 2 by actuating the deployment mechanism 40. In particular, the plunger 66 may be actuated to deploy the cuff 42 at the fixed axial location L. As described above, an internal catheter engagement surface 46 of the hollow cylindrical body 44 of the cuff 42 may be adhered to an external surface 50 of the elongate tubular body 14 of the catheter 12 at the fixed axial location L using an adhesive 48. Additionally, or alternatively, the hollow cylindrical body 44 of the cuff 42, which may include a self-expanding stent, may be radially expanded during the deployment to assist in maintaining the desired positioning of the cuff 42 relative to the catheter 12. After the cuff 42 has been deployed, the cuff deployment device 38 may be removed from the elongate tubular body 14 of the catheter 12 at the open distal end 22 thereof.

To tunnel the catheter assembly 10 for long-term vascular access, the clinician may make a first incision at or near the lower neck to gain access to the vascular structure 90. A second incision may be made below the first incision and a subcutaneous tunnel 94 between the incisions may be created. A tunneled portion 92 of the catheter assembly 10 may be positioned in the subcutaneous tunnel 94, using known techniques, with the cuff 42 positioned at a desired location within the tunneled portion 92. For example, it may be desirable to position the cuff 42 at a medial location 96 along the tunneled portion 92 of the catheter 12. The porous ingrowth material 80 of the hollow cylindrical body 44 of the cuff 42 may promote tissue growth into the cuff 42 to secure the positioning of the catheter assembly 10.

The catheter assembly 10 provided herein, including the cuff deployment device 38, may be used as an indwelling tunneled catheter for long-term vascular access. As described, the cuff deployment device 38 permits a clinician to selectively deploy the cuff 42 at a desired axial location L, which may vary depending on the specifics of the patient, tunnel size and configuration, and procedure being performed. The variable deployment eliminates the need to trim the catheter 12 to achieve a desired cuff-to-distal tip distance, which may not be apparent until after commencement of the procedure. After the cuff 42 has been deployed, the cuff deployment device 38 may be removed from the catheter assembly 10, eliminating the need for additional structures or components of the indwelling tunneled catheter.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A catheter assembly, comprising:
   a catheter having an elongate tubular body with an external surface and defining a lumen extending from an open proximal end of the elongate tubular body to an open distal end of the elongate tubular body;
   a cuff deployment device concentrically supported on the elongate tubular body and movable along a longitudinal axis of the elongate tubular body, wherein the cuff deployment device includes a deployment mechanism having an actuated position and a non-actuated position;
   a cuff having a hollow cylindrical body defining an internal catheter engagement surface for contacting the external surface of the elongate tubular body;
   wherein the catheter assembly has a first configuration in which the deployment mechanism is in the non-actuated position and the cuff is supported by and movable with the cuff deployment device, and a second configuration in which the deployment mechanism is in the actuated position and the cuff is concentrically mounted at a fixed axial location of the elongate tubular body and is free of contact with the cuff deployment device; and
   wherein the cuff deployment device is out of contact with the internal catheter engagement surface in both the actuated position and the non-actuated position.

2. The catheter assembly of claim 1, wherein the cuff deployment device includes a cylindrical housing configured to telescopically receive the cuff and having an open proximal deployment end and a distal end, and wherein the deployment mechanism includes a tubular plunger with an outwardly extending flange and having an actuation end configured to contact the cuff through the distal end of the cylindrical housing.

3. The catheter assembly of claim 1, further including an adhesive provided on the internal catheter engagement surface of the cuff, wherein the adhesive contacts an external surface of the elongate tubular body in the second configuration of the catheter assembly.

4. The catheter assembly of claim 1, wherein the hollow cylindrical body of the cuff includes a porous tissue ingrowth material.

5. The catheter assembly of claim 4, wherein the hollow cylindrical body of the cuff is configured to radially expand in the second configuration of the catheter assembly.

6. The catheter assembly of claim 5, wherein the hollow cylindrical body of the cuff also includes a shape memory material.

7. The catheter assembly of claim 1, further including a concentrically mounted end stop positioned distally along the elongate tubular body relative to the cuff deployment device and configured to restrict distal movement of the cuff deployment device beyond the end stop in the first configuration of the catheter assembly.

8. The catheter assembly of claim 1, wherein the catheter is an indwelling tunneled catheter.

9. The catheter assembly of claim 1, wherein the catheter assembly has a third configuration in which the cuff is concentrically mounted at the fixed axial location of the elongate tubular body and the cuff deployment device is removed from the elongate tubular body.

10. A cuff deployment device for a catheter assembly, comprising:
    a hollow cylindrical housing having an open proximal deployment end and a distal end;
    a tubular plunger with an outwardly extending flange and defining an inner catheter engagement surface and having an actuation end supported within an opening through the distal end of the hollow cylindrical housing, wherein the tubular plunger is telescopically movable with respect to the hollow cylindrical housing;
    a cuff having a hollow cylindrical body defining an internal catheter engagement surface for contacting an external surface a catheter, and the cuff being telescopically received within the hollow cylindrical housing.

11. The cuff deployment device of claim 10, further including an adhesive provided on the internal catheter engagement surface of the hollow cylindrical body of the cuff.

12. The cuff deployment device of claim 11, wherein the hollow cylindrical body of the cuff includes a porous ingrowth material.

13. The cuff deployment device of claim 12, wherein the hollow cylindrical body of the cuff is configured to radially expand.

14. The cuff deployment device of claim 13, wherein the hollow cylindrical body of the cuff also includes a shape memory material.

15. A method of implanting a catheter assembly in a patient vasculature, the catheter assembly including: a catheter having an elongate tubular body with an external surface and defining a lumen extending from an open proximal end of the elongate tubular body to an open distal end of the elongate tubular body; a cuff deployment device concentrically supported on the elongate tubular body and movable along a longitudinal axis of the elongate tubular body, wherein the cuff deployment device includes a deployment mechanism having an actuated position and a non-actuated position; and a cuff having a hollow cylindrical body defining an internal catheter engagement surface for contacting the external surface of the elongate tubular body; wherein the catheter assembly has a first configuration in which the deployment mechanism is in the non-actuated position and the cuff is supported by and movable with the cuff deployment device, and a second configuration in which the deployment mechanism is in the actuated position and the cuff is concentrically mounted at a fixed axial location of the elongate tubular body and is free of contact with the cuff deployment device, and wherein the cuff deployment device is out of contact with the internal catheter engagement surface in both the actuated position and the non-actuated position, the method comprising steps of:
    sliding the cuff deployment device toward the fixed axial location while the catheter assembly is in the first configuration;
    moving the catheter assembly from the first configuration to the second configuration at least in part by actuating the deployment mechanism; and
    removing the cuff deployment device from the elongate tubular body of the catheter.

16. The method of claim 15, further including adhering the internal catheter engagement surface of the hollow cylindrical body of the cuff to an external surface of the elongate tubular body of the catheter at the fixed axial location.

17. The method of claim 15, further including radially expanding the hollow cylindrical body of the cuff during the step of moving the catheter assembly from the first configuration to the second configuration.

18. The method of claim 17, further including radially expanding the hollow cylindrical body of the cuff using a shape memory material of the hollow cylindrical body of the cuff.

19. The method of claim 15, further including tunneling a tunneled portion of the catheter through a subcutaneous tunnel of the patient with the cuff positioned at a medial location along the tunneled portion of the catheter.

20. The method of claim 19, further including promoting tissue ingrowth with a porous ingrowth material of the hollow cylindrical body of the cuff.

* * * * *